United States Patent [19]

Janata et al.

[11] 4,175,020
[45] Nov. 20, 1979

[54] METHOD OF STERILIZING REFERENCE ELECTRODES AND THE LIKE

[75] Inventors: Jiri Janata; Paul T. McBride, both of Salt Lake City, Utah

[73] Assignee: University of Utah, Utah

[21] Appl. No.: 949,573

[22] Filed: Oct. 10, 1978

[51] Int. Cl.² .................. A61L 1/00; G01N 27/30
[52] U.S. Cl. ..................... 204/195 B; 204/195 F; 422/28; 422/34
[58] Field of Search ............... 422/28, 34; 204/195 F, 204/1 T, 195 B; 128/2 E

[56] References Cited

U.S. PATENT DOCUMENTS

| | | | |
|---|---|---|---|
| 3,257,161 | 6/1966 | Kaye | 422/28 X |
| 3,844,275 | 10/1974 | Elliot | 204/195 B X |
| 4,020,830 | 5/1977 | Johnson et al. | 128/2 E |

*Primary Examiner*—G. L. Kaplan
*Attorney, Agent, or Firm*—Criddle, Thorpe & Western

[57] ABSTRACT

A reference electrode having a first tubular member, an elongate electrode element disposed within the tubular member, and a second tubular member disposed within the first tubular member to protrude out one end thereof is sterilized by aspirating through the first tubular member into the second tubular member a solution of HEMA and a salt dissolved in a solvent, evaporating the solvent, exposing the interior and exterior surfaces of the electrode to ethylene oxide gas, aerating the electrode, and immersing the electrode in a solution of said salt until the osmolality of the solution within the electrode and of the solution without the electrode is substantially the same.

7 Claims, 1 Drawing Figure

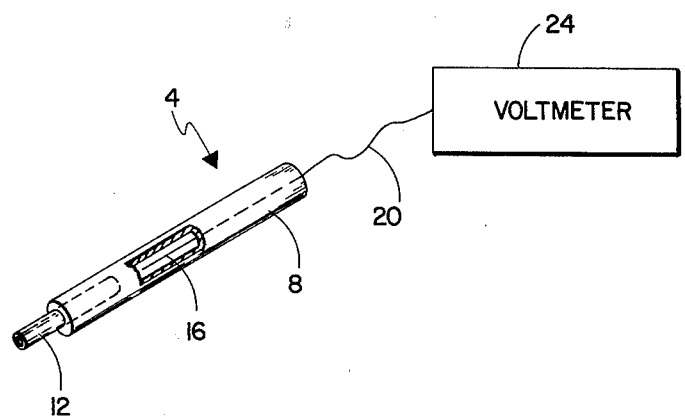

METHOD OF STERILIZING REFERENCE ELECTRODES AND THE LIKE

BACKGROUND OF THE INVENTION

This invention was funded in part by a Dept. of H.E.W. grant no. NIGMS 22952.

This invention relates to a method of sterilizing tubular electrode structures or the like.

Reference electrodes are used in a variety of situations where detection, measurement or monitoring of chemical properties is to be carried out. Such chemical properties might include ion activity and concentration, presence and concentration of enzymes, substrates, antibodies, antigens, hormones and reducible gases and the presence, concentration and activity of any of a variety of other chemical and biochemical substances. An example of the use of a reference electrode in a device capable of detecting such chemical properties is described in U.S. Pat. No. 4,020,830. As discussed in the referenced patent, this device is capable of in vivo measurement of various chemical and biochemical properties of substances to which the device is eposed. Of course, in order to use such a device for in vivo measurement, the parts of the device including the reference electrode should be sterile so that the possibility of infection is minimized.

Sterilization of reference electrodes which utilize a liquid junction connection can be difficult because of the construction of the electrode, such construction typically including a single tube with an electrode element disposed in the tube. Chemical sterilization would be suitable for such electrodes provided the sterilizing chemicals could be readily introduced into the tube, removed from the tube and then a sterile liquid junction medium introduced back into the tube. However, such a process is difficult both from the standpoint of introducing the sterilizing chemical into the tube, removing the chemical from the tube and then maintaining the sterility of the liquid junction medium as is introduced into the tube. Radiation or high temperature sterilization is an alternative but if the reference electrode is an integral part of the measuring device, then damage to the device might result.

SUMMARY OF THE INVENTION

It is an object of the invention to provide a simple method of sterilizing reference electrodes or similar structures which utilize liquid junctions for making electrical contact with a substance.

It is a further object of the invention to provide such a method which may penetrate cavities housing an electrode element.

It is an additional object of the invention to provide such a method for sterilizing reference electrodes without damaging other parts of the measuring device.

The above and other objects of the invention are realized in a specific illustrative embodiment of a method for sterilizing reference electrodes in which the electrode element is in a cavity, access to which is through a capillary. The method includes delivering into the cavity of the electrode a first solution of a salt and hydroxyethylmethacrylate dissolved in an organic solvent, evaporating the solvent from the solution, exposing the interior and exterior surfaces of the electrode to a sterilizing gas such as ethyleneoxide, aerating the electrode and then immersing the electrode in or otherwise applying to the electrode a sterile second solution of the same salt. The capillary of the reference electrode operates to pull this second solution into the cavity and, after a time, the osmolality of the solution within the cavity is substantially the same. The electrode is then ready for use.

BRIEF DESCRIPTION OF THE DRAWINGS

The above and other objects, features and advantages of the present invention will become apparent from a consideration of the following detailed description presented in connection with the accompanying drawing which shows a perspective, partially cut away view of a reference electrode which may be sterilized using the method of the present invention.

DETAILED DESCRIPTION

The drawing shows a reference electrode 4 which includes a first or outer tubular member 8 and a second or inner tubular member 12 which is inserted in one end of the member 8. The inner tubular member 12 has interior dimensions (e.g. 30 to 50 microns in diameter) suitable to enable it to act as a capillary. The tubular member 12 need not protrude out the end of the member. Other shapes for the "capillary" besides the tubular shape could also be used.

An electrode element 16 in the form of a wire is disposed within the tubular member 8 to extend from the rear of the member toward, but just short of, the end of the member in which the inner tubular member 12 is disposed. The rear end of the inner tubular member 12 terminates near the point of termination of the electrode element 16. The electrode element 16 is coupled by a conductor 20 to a voltmeter 24.

The electrode element 16 may be constructed of a silver wire coated with silver chloride (if chloride solutions, as hereafter discussed, are used), or other suitable conductive material. The tubular members 8 and 12 are constructed of electrically nonconducting material such as glass, various plastics, etc.

The reference electrode 4 is filled with a solution so that during measurement of a substance, a liquid junction can be formed between the solution and the substance. The method of sterilizing the reference electrode and of filling the electrode with the liquid junction solution will next be described.

The first step in sterilizing and preparing the reference electrode for use is to aspirate into the reference electrode compartment through the tubular member 12 a solution of salt (such as sodium chloride) and hydroxyethylmethacrylate (HEMA) dissolved in an organic solvent (such as methanol). This can be done by applying a moderate vacuum to the rear end of the tubular member 8 and then immersing the tubular member 12 in the solution. After the reference electrode compartment is filled at least to a point where the electrode element 16 is surrounded by the solution, the organic solvent is evaporated such as by heating to leave a residual of salt and HEMA. The dry reference electrode is then exposed to a sterilizing gas such as ethylene oxide for a period of time so that both the exterior and interior surfaces of the electrode are contacted by the gas. The electrode is then aerated until dry and then a sterile salt solution is applied to the reference electrode such as by immersing the reference electrode in the solution. The presence of the tubular member 12 results in a capillary action whereby salt solution is drawn through the tubular member 12 into the interior of the electrode 4. The concentration of salt inside the compartment (resulting from the earlier evaporation of the solvent) is initially very high and consequently the osmotic pressure difference between the interior of the reference electrode and the salt solution in which the electrode is immersed forces more water into the electrode. The flow of solution into the electrode will continue until the osmotic pressure difference substantially vanishes, i.e., until the concentration of salt within the electrode 4 is substantially the same as the concentration outside the electrode. When this point is reached, the reference electrode is sterile and ready for use.

As an example of the use of the above procedure for the preparation of sterile reference electrodes, a 0.15 molar solution of sodium chloride and methanol which included 1% by weight hydroxyethylmethacrylate was aspirated into the reference electrode compartment through the tubular member 12. The aspiration of this solution into the electrode interior was accomplished by applying a moderate vacuum to the rear end of the tubular member 8. The reference electrode was then placed in a vacuum oven at 50° centigrade for a period of 12 hours which sufficed to evaporate the methanol from the electrode, after which the electrode was exposed to ethylene oxide for a period of three hours and then aerated for a period of 12 hours. The reference electrode was then immersed in a sterile 0.15 molar solution of sodium chloride dissolved in water. Immersing the reference electrode in the saline solution, as before indicated, resulted in the exhibition of a capillary action by the inner tubular member 12 to draw the saline solution into the interior of the electrode. The reference electrode was left in the saline solution for about 2 hours.

Electrodes sterilized and charged using the above process have been tested by connecting them to an electrometer, placing them in a conducting solution, and recording the potential difference against conventional reference electrodes. The time required for the reference electrode to make electrical contact with the solution in which it is placed is about five minutes, after which the electrode drifts for about two hours and then became stable to within <0.2 mV/hr. That is, the potential difference between the subject reference electrode and the conventional reference electrode drifts less than 0.2 mV/hr.

The method of sterilizing reference electrodes and similar structures in accordance with the present invention is simple and yet certain. Provision of a reference electrode having a capillary in one end facilitates "reconstitution" of the reference electrode with the solution which will be used to make the liquid junction contact with a measured solution. Although particular ingredients for the different solution components were given, it should be understood that a variety of different salts could be used and a variety of different organic solvents. The requirement of the first solution used is simply that the salt and HEMA be dissolved in the solvent and the requirement of the second solvent used is that the salt be dissolved in the water.

The concentration of HEMA in the solvent may vary from about 0.75 to 1.5% by weight with concentrations of about 1% by weight being preferable. However, higher or lower ranges of HEMA concentrations which are operative are also within the scope of this application.

Any inorganic salt may be used which is soluble in the solvent and in water at the concentration levels used. The particular salt chosen is not critical as long as the same salt is used throughout the sterilization process. Concentrations are preferably rather dilute ranging from about 0.05 to 0.5 molar. However, higher or lower concentrations are not precluded. Alkali, alkaline earth and transition metal salts may all be used. Because of their ready availability and solubility in water and organic solvents, metal chlorides and particularly alkali and alkaline earth metal chlorides are preferred.

The particular solvent employed is not critical as long as it will dissolve HEMA and the salt. Since the solvent must be evaporated the boiling point is preferably below about 100° C. Typical solvents include alcohols and ketones having from one to four carbon atoms such as methanol, ethanol, acetone and methyl ethyl ketone.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method of sterilizing and charging a reference electrode comprising
   providing a reference electrode which includes a tubular member open at least at one end, and an electrode element disposed in said tubular member, said one end being formed to function as a capillary,
   delivering into the tubular member to surround said electrode element a first solution of a certain salt and hydroxyethylmethacrylate dissolved in an organic solvent,
   evaporating the solvent from the first solution,
   exposing the surfaces of the reference electrode to a sterilizing gas,
   aerating the reference electrode, and
   applying a sterile second solution of said certain salt to the reference electrode until the osmolality of the solution within the tubular member and the second solution is substantially the same.

2. A method as in claim 1 wherein said delivering step comprises aspirating the first solution into the tubular member.

3. A method as in claim 1 wherein said first solution contains 0.75% to 1.5% hydroxyethylmethacrylate by weight.

4. A method as in claim 1 wherein said solvent is methanol.

5. A method as in claim 1 wherein said evaporating step comprises placing the reference electrode in a vacuum oven and heating the electrode for a time sufficient to evaporate the first solvent.

6. A method as in claim 1 wherein the sterilizing gas used in said exposing step is ethylene oxide.

7. A method as in claim 1 wherein said applying step comprises immersing the reference electrode in said second solution.

* * * * *